United States Patent [19]

Robins et al.

[11] Patent Number: 5,461,079
[45] Date of Patent: Oct. 24, 1995

[54] ANTIFUNGAL COMPOUNDS

[75] Inventors: David J. Robins, Glasgow; Dale R. Walters, Ayrshire, both of Scotland

[73] Assignee: British Technology Group Limited, London, England

[21] Appl. No.: 150,095

[22] PCT Filed: May 28, 1992

[86] PCT No.: PCT/GB92/00963

§ 371 Date: Nov. 19, 1993

§ 102(e) Date: Nov. 19, 1993

[87] PCT Pub. No.: WO92/21235

PCT Pub. Date: Dec. 10, 1992

[30] Foreign Application Priority Data

May 31, 1991 [GB] United Kingdom .............. 9111794

[51] Int. Cl.$^6$ .............................................. A01N 33/02
[52] U.S. Cl. .............................................. 514/671
[58] Field of Search .............................................. 514/671

[56] References Cited

U.S. PATENT DOCUMENTS

| 4,201,788 | 5/1980 | Vorhees et al. | 424/304 |
| 4,207,315 | 6/1980 | Voorhees et al. | 424/200 |
| 4,760,091 | 7/1988 | Carson et al. | 514/561 |

FOREIGN PATENT DOCUMENTS

| WO88/02986 | 5/1988 | WIPO . |
| WO92/21236 | 12/1992 | WIPO . |

OTHER PUBLICATIONS

N. Seiler et al., "Diamine oxidase and Polyamine Catabolism", Advances in Polyamine Research vol. 4, ed. U. Bachrach et al., Raven Press N.Y. (1983), pp. 135–154.
S. Sarhan et al., "Putrescine derivatives as substrates of spermidine synthase", Int. J. Biochem. 19, 1037–1047 (1987).
L. Macholan et al., "Oxidation of 1,4–diamino–2–butene to pyrrol . . . ", Coll. Czech. Chem. Commun. 40, 1247–1256 (1975).
L. H. Amundsen et al., "The Action of Ammonia and Amines on 1,4–dichloro–2–butene", J. Amer. Chem. Soc. 73, 2118–2121 (1951).
N. Relyea et al. "Potent inhibition of ornithine . . . " Biochem & Biophysical Comm, vol 67 No. 1 (1975), pp. 392–403.
T. A. Smith et al. "Growth inhibition of . . . " Jour of Gen Microbiol (1990) 136, pp. 985–992.
Chemical Abstracts, vol. 84 No. 1, 5 Jan. 1976 Abstract #1710. Relyea, N. et al "Potent Inhibition . . . ".
S. Foster & D. R. Walters, "The effects of polyamine biosynthesis inhibitors on mycelial growth, enzyme activity and polyamine levels . . . ", J. Gen. Microbiol., 136, 233–239 (1990).
D. Walters, "Polyamines and plant disease", Plants Today, 22–26 (Jan.–Feb. 1989).
A. E. Pegg et al., "Polyamine Metabolism and Function in Mammalian Cells and Protozoans", ISI Atlas of Science: Biochemistry, 11–18 (1988).
D. Walters, "Polyamines: the Cinderellas of cell biology", Biologist 34 (2), 73–76 (1987).
N. D. Havis et al., "In vitro effects of the polyamine biosynthesis inhibitor, α–difluoromethylornithine, on ornithine decarboxylase activities . . . ", letters in Applied Microbiology 14, 244–246 (1992).
M. V. Rajam et al., "Effect of polyamine biosynthesis inhibitors on polyamine levels in bean seedlings", Current Science 60 (3), 178–180 (Feb. 1991).

Primary Examiner—Allen J. Robinson
Attorney, Agent, or Firm—Nixon & Vanderhye

[57] ABSTRACT

The use of (E)-2-butene-1,4-diamine or a salt thereof with inorganic or organic acids, as a fungicide.

9 Claims, No Drawings

ANTIFUNGAL COMPOUNDS

This application is a 371 of PCT/GB 92/00963 filed May 28, 1992.

FIELD OF THE INVENTION

This invention is in the field of the control of fungal infection in plants.

DESCRIPTION OF THE PRIOR ART

Polyamines are essential for the growth and development of all organisms, including plants and fungi. However, whereas plants possess two pathways for polyamine biosynthesis, i.e. via the enzymes ornithine decarboxylase [ODC] and arginine decarboxylase [ADC], fungal polyamine biosynthesis appears to be a result of ODC activity only.

Plants are attacked by a wide range of fungi which are the cause of considerable losses of yield and quality. Since fungi possess only the ODC pathway of polyamine biosynthesis, the inhibition of this enzyme should control their growth.

Such inhibitors have been extensively researched but the major breakthrough was directly attributable to the synthesis of enzyme-activated irreversible inhibitors of ODC and ADC notably difluoromethylornithine [DFMO], which has been tested as an anti-cancer agent and also as an anti-parasitic agent, and difluoromethylarginine [DFHA].

Recent work has shown that DFHO can reduce fungal growth and has led to the investigation of the use of DFMO as a fungicide, see for example WO88/02986 (Heinstein and Galston) and U.S. Pat. No. 4,760,091 (Carson et al.).

The effect of compounds (including DFMO) which interfere with polyamine metabolism on the growth of the fungus *Botrytis cinerea* has been investigated (Smith et al., J. Gen. Microbiol. 1990, 136, 985). This work demonstrated that the DFMO inhibition of fungal growth could be reversed with the addition of putrescine, cadaverine, spermidine and spermine. "Butenediamine", caused some inhibition of fungal growth but significantly reversed the inhibitory effect of DFMO.

SUMMARY OF THE INVENTION

It has surprisingly been found that the diamine (E)-2-butene-1,4-diamine (the trans isomer) exhibits considerable anti-fungal activity. Accordingly, the invention provides the use as a fungicide of (E)-2-butene-1,4-diamine.

The diamine may also be used as a salt with organic or inorganic acids.

DESCRIPTION OF THE PREFERRED EMBODIMENTS

The antifungal activity of (E)-2-butene-1,4-diamine is thought to be due mainly to its properties of polyamine metabolism interference. However, other mechanisms may play a role in the activity of this compound as an antifungal agent which cannot be ruled out at this stage.

(E)-2-butene-1,4-diamine may be synthesised and isolated as a salt using the conventional techniques of synthetic organic chemistry. The preferred syntheses are those which use (E) starting materials and yield exclusively the trans-diamine, i.e. in which substantially all of the diamine produced is the trans-diamine.

The diamine may comprise a minor proportion of the (Z) (cis) isomer say up to 10% or even 25% but the use of such mixtures is less preferred as the cis isomer is less effective than the corresponding trans isomer.

(E)-2-butene-1,4-diamine may be synthesised as its dihydrochloride salt from (E)-1,4-dibromobut-2-ene by conversion into the bisphthalimide with potassium phthalimide followed by acid hydrolysis. It may also be prepared by heating (E)-1,4-dibromobut- 2-ene at reflux in benzene with sodium azide in the presence of tetrabutylammonium bromide, subsequent addition of triethyl phosphate and treatment with dry hydrogen chloride, according to the method of Koziara et al., Synthesis 1985, 202. Another synthesis which may be employed is that reported by L. H. Amundsen et al., J. Am. Chem. Soc. 1951, 73, 2118 which utilises the trans form of butene-1,4-diol rather than the cis form used by Amundsen. (E)-2-butene-1,4-diamine also exhibits antifungal activity when prepared in the form of its acid salts and such salts may be utilised as fungicides according to this invention. The compound can form salts with mineral acids such as HCl, HBr, HI, $H_2SO_4$, $HNO_3$, $H_3PO_4$ or with organic acids such as formic, acetic, trifluoroacetic, propionic, benzoic, maleic, fumaric, succinic, tartaric, citric, oxalic, glyoxylic, alkyl- or aryl-sulphonic, salicylic, malonic and ascorbic. These salts may be prepared by standard techniques and procedures well known in the art.

The present invention also provides a method for the fungicidal treatment of plant material in either a preventative or curative mode. The treatment may be applied to growing or harvested plant materials. If the plant material is growing, then the plants may be treated before they are infected by the fungi. This can be carried out by either treating the whole plant (e.g. by spraying it with a solution/emulsion or suspension of the antifungal compounds) or on specific parts of the plant, e.g. the leaves, stems, fruits or even seeds prior to planting. Treatment of the soil is another alternative since the antifungal compounds of the invention are systemic in their mode of action. Plants which have come into contact with fungi and thus already infected may be treated locally at site of infection or the whole plant may be treated.

The present invention also includes treatment of harvested plant parts for the control of fungal diseases. For this, various ways of carrying out the treatment can be employed. These will be well known to those skilled in the art, for example, treatment can be to the harvested plant itself by for example dipping the plant part into a solution of the antifungal agent, or by impregnating fungicide into the plant packaging material, e.g. wrapper, carton, crate, etc. in which the plant will be transported. Alternatively, the harvested plant material may be fumigated with the fungicide in a special room, car or tank.

This invention also provides fungicidal compositions comprising (E)-2-butene-1,4 diamine together with a suitable diluent or carrier. Such diluents or carriers must not be phytotoxic to the plant materials. Suitable diluents and carriers include water and organic solvents. Preferably the concentration of (E)-2-butene-1,4-diamine is between 0.001–0.1 molar.

Seeds may be treated prior to planting and again this may be carried out among other methods by fumigation.

Thus, the diamine can be dispersed on a finely-divided solid to form a dust. Also, the diamine can be dispersed in water, typically with the aid of a wetting agent, and the resulting aqueous dispersion employed as a spray. In other procedures the diamine can be employed as a constituent of organic liquid compositions, oil-in-water and water-in-oil emulsions or dispersions, with or without the addition of wetting, dispersing or emulsifying agents.

Suitable adjuvants of the foregoing type are well known to those skilled in the art. The methods of applying the solid or liquid fungicidal formulations are similarly well known.

The concentration of the active compounds in solid or liquid compositions generally is from about 1 to about 20 percent by weight or more. Concentrations from about 5 to about 10 percent by weight are often employed. In concentrated compositions which are diluted prior to use, the active compound can be present in a concentration from about 15 to about 50 weight percent, preferably 20 weight percent. The compositions containing the active compounds can also contain other compatible additives, for example, phytotoxicants, plant growth regulators, pesticides, other fungicides and the like which are suitable for application to agricultural, horticultural, forestry and amenity crops. The present compositions can be applied by the use of power dusters, boom and hand sprayers, spray dusters and by other conventional means. The compositions can also be applied from airplanes as a dust spray since the ingredients are effective at very low application rates.

The exact rate to be applied Is dependent not only on the specific diamine being applied, but also on the particular treatment desired (e.g. seed, soil, or foliage) the particular crop being treated, climatic conditions, severity of any infection and the like. Thus, it is also to be understood that all of the active compounds of the present invention and compositions containing the same may not be equally effective at similar concentrations or against the same fungal species.

In foliar treatments, the active compounds of the present invention are usually applied at an approximate rate of from about 50 to 500 g/ha, a rate of from about 80 to 400 g/ha being preferred and a rate of from about 100 to about 350 g/ha being particularly preferred.

In seed treatments, the active compounds of the present invention are usually applied at an approximate rate of from about 60 to about 250 g per 100 kg seed, a rate of from about 100 to about 200 g per 100 Kg seed being preferred and a rate of from about 140 to about 180 g per 100 kg seed being particularly preferred.

In soil treatments, the active compounds of the present invention are usually applied at an approximate rate of from about 50 to about 350 g/ha, a rate of from about 100 to about 300 g/ha being preferred and a rate of from about 200 to about 280 g/ha being particularly preferred.

A typical solid composition Is formulated by dry milling the active compound with BARDEN clay. This solid formulation or dust can contain the active compounds in amounts of from about 1 to about 25 percent by weight or more if desired. The dust is suitable for application to cereal seeds prior to planting.

A typical liquid composition is formulated by dissolving the active compound in a mixture of water and isopropanol (80:20 water/isopropanol ratio) containing a surfactant. This liquid formulation can contain the active compound in amounts of from about 15 to about 40 percent by weight or more if desired. The aqueous formulation is suitable for application to cereal foliage or application as a seed drench, after suitable dilution with water.

The invention will now be illustrated by the following Examples.

EXAMPLE 1

Synthesis of (E)-1,4-Diaminobut-2-ene (E-BED) Dihydrochloride

This synthesis was carried out by adapting the procedure of L. Macholan, Coll. Czech. Chem. Commun., 1974, 39, 653.

Potassium phthalimide (20 g, 108 mmol) was added in portions over 2 h to a stirred solution of (E)-1,4-dibromobut-2-ene (10.7 g, 50 mmol ) in DMF (100 ml) at room temperature. The mixture was stirred for a further 3 d at this temperature, then poured into water (100 ml), and the mixture was extracted with dichloromethane (5×100 ml). The organic extracts were dried, filtered and concentrated in vacuo to leave DMF (ca. 30 ml), and a white solid, which was filtered off and washed with ether (3×10 ml) to give (E)-1,4-diphthalimidobut-2-ene (15.75 g, 91%). $\delta_H$ (90 MHz, CDCl$_3$) 4.28 (4H, d), 5.92 (2H, m), and 7.79 (4H, m).

(E)-1,4-Diphthalimidobut-2-ene (15.72 g, 45 mmol) was suspended in glacial acetic acid (160 ml), and conc. HCl (160 ml) was added. The mixture was heated at reflux until all the (E)-1,4-diphthalimidobut-2-ene had dissolved, than for a further 24 h. The solution was cooled, filtered, and the solvents were concentrated in vacuo to ca. 10 ml. The precipitate was collected and washed with ether to afford (E)-1,4-diaminobut-2-ene dihydrochloride (6.48 g, 90%) $\delta_H$ (90 MHz, D$_2$O) 3.96 (4H, d) and 5.78 (2H, m).

EXAMPLE 2

Synthesis of (E)-1,4-Diaminobut-2-ene and Salts (E)-1,4-Diaminobut-2-ene dihydrochloride (1.21 g, 7.6 mmol) was dissolved in the minimum amount of water (10 ml), added to ether (100 ml) and stirred vigorously. Potassium carbonate (40 g) was added and the stirring was continued for 0.5 h. The solid was filtered off, and the filtrate was concentrated in vacuo to give (E)-1,4-diaminobut-2-ene as an oil (0.46 g, 70%). $\delta_H$ (90 MHz, CDCl$_3$) 1.80 (4H, s), 3.3 (4H, m) and 5.7 (2H, m).

(E)-1,4,-Diaminobut-2-ene (1 equiv.) was stirred with benzoic acid (2 equiv.) in benzene for 1 h. The precipitate was filtered and washed with ether to afford a white solid (68%). $\delta_H$ (200 MHz, D$_2$O) 3.46 (4H, m), 5.78 (2H, m) and 7.38 (10H, m).

Other compounds were prepared by this method.

E-BED phosphate (2.81 g, 85%). $\delta_H$ (90 MHz, D$_2$O) 3.50 (4H, s) and 5.85 (2H, m).

E-BED fumarate (0.75 g, 70%) $\delta_H$ (200 MHz, D$_2$O) 3.48 (4H, m), 5.80 (2H, m) and 6.51 (4H, m).

E-BED propionate (0.41 g, 83%) $\delta_H$ (200 MHz, D$_2$O) 0.84 (6H, t), 1.99 (4H, q), 3.41 (4H, m) and 5.72 (2H, m).

EXAMPLE 3

The effects of two putrescine analogues Z-BED (cis-1,4-diaminobut- 2-ene dihydrochloride) and E-BED, (trans-1,4-diaminobut-2-ene dihydrochloride) on the growth of Botrytis cinerea An experiment was performed to determine the effects of E-BED and Z-BED on the growth of Botrytis cinerea in vitro. The experiments were performed as described by Smith et al., (1990, J.G.M. 136 985–992). In Smith et al., the chemical, synthetic and biological evidence for "butenediamine" is consistent with a cis isomer. The results are shown in Table 1 below.

TABLE 1

| Treatment | Fungal growth, mm |
|---|---|
| Control | 17.0 ± 1.2 |
| E-BED, 1 mM | 2.2 ± 0.3 |
| Z-BED, 1 mM | 7.4 ± 0.9 |

1 mM E-BED reduced the growth of *B. cinerea* by 87%, while Z-BED reduced fungal growth by 58%.

EXAMPLE 4

The effect of E-BED and Z-BED on the growth and polyamine biosynthesis of *P. avenae*.

*Pyrenophora avenae* was an ideal fungus for studying the effects of inhibitors on polyamine biosynthesis because it was moderately sensitive to the putrescine analogues (inhibitors) and there was sufficient fungal growth for detailed biochemical analyses [Foster and Walters, J. Gen. Microbiol. 136, 233, 1990].

Method

Growth in liquid media: Ten ml aliquots of filter-sterilized solution containing the inhibitor were added to 140 ml sterile liquid PDA (potato dextrose agar), in 250 ml flasks, to obtain the following concentrations: 0.5 mM Z-BED and 0.5 mM E-BED. Each flask was inoculated with a 10 mm disc of mycelium and placed in an orbital shaker at 140 rpm, at 24° C. After 4 days the fungus was washed with distilled water through a fine mesh sieve and centrifuged at 14,000 rpm for 10 min. The pellet obtained was used for enzyme and polyamine analyses.

Enzyme Assays: Crude enzyme extracts were prepared by grinding 500 mg fungus $ml^{-1}$ buffer using a prechilled pestle and mortar. Buffers used were as described by Stevens et al. (Biochem. J. 1976, 158, 235–241). The suspensions were sonicated using a Soniprep 150 for 10 cycles of 10 s on/20 s off. Test-tubes were kept on ice during sonication. Each sample was centrifuged at 17,000 rev $min^{-1}$ for 15 min at 0° C. For ornithine decarboxylase assays, the supernatant (cytosolic fraction) was dialysed against 30 vol of buffer for 24 h in the dark. The pellet (nuclear fraction) was redissolved in original volume of buffer and dialysed as above.

For S-adenosylmethionine decarboxylase assays, 430 mg $(NH_4)_2SO_4$ was added to 1 ml supernatant and redissolved pellet (cytosolic and nuclear fractions respectively). The suspensions were centrifuged at 17,000 rev min $^{-1}$ for 20 min at 0° C. The pellets obtained were redissolved In original volume of buffer and dialysed as previously described. Enzyme activities were assayed by measuring $^{14}CO_2$ released after incubation with $[1-^{14}C]$-ornithine and S-adenosyl$[1-^{14}C]$-methionine for ornithtne decarboxylase and S-adenosylmethionine decarboxylase respectively. Radioisotopes were obtained from Amersham International plc. The reaction mixtures used were as described by Stevens et al. (1976).

Assays were carried out in 98 mm glass test-tubes fitted with silicone rubber stoppers (Vacutainer, UK) and 35 mm long, 22-gauge needles. A piece of filter paper 10 mm in diameter, impregnated with 10 μl 2M KOH was fitted to each needle to trap $^{14}CO_2$ released during the reaction. The test-tubes were placed in a water bath at 37° C. for 30 minutes after which 0.2 ml of 6% (v/v) $HClO_4$ was injected into each tube and incubated for a further 30 min. The filter paper was then removed and placed in a scintillation vial containing 12 ml Emulsifier-safe scintillant. The samples were counted for radioactivity using a LKB 1215 RACK-BETA Liquid Scintillation counter. Activity was expressed as pmol $^{14}CO_2$ (mg protein)$^{-1}$ $h^{-1}$. Protein assays were carried out using the method of Lowry using bovine serum albumin as standard. All results are the means of 5 replicates. Significance was assessed using Students' t-test.

Polyamine analysis: 600 mg of fungus was macerated with 1 ml 4% (v/v) $HClO_4$. The samples were sonicated as described for enzyme assays, then centrifuged at 12,000 rev $min^{-1}$ for 25 min at 0° C. To each 200 μl aliquot of supernatant, 17 mg of $Na_2CO_3$ and 400 μl dansyl chloride (30 mg $μl^{-1}$ acetone) were added. This mixture was incubated in darkness overnight at 22° C. Excess dansyl chloride was converted to dansyl proline by incubating for 30 minutes with 0.1 μl L-proline (100 mg $ml^{-1}$). The dansylated polyamines were extracted in 250 μl toluene. 25 μl aliquots of the toluene extract were spotted onto activated LK6D silica-gel plates (Whatman) and left to develop in tanks containing chloroform: triethylamine (5:1 (v/v)). The spots were traced using a UV lamp, cut out and the dansylated derivatives extracted in 5 ml ethyl acetate. Standards between 0.1–10 μg were measured. Fluorescence was measured in a Perkin-Elmer LS-5 luminescence spectrometer at excitation 365 nm, emission 506 nm. Polyamines were expressed as nmol $(g.f.wt)^{-1}$. All results are the means of 4 replicates. Significance was assessed using the Students' t-test.

Results

The results are shown In Tables 2 and 3 below.

TABLE 2

The effects of Z-BED and E-BED on enzyme activity in *Pyrenophora avenae*

| | Mycelial growth g | ODC activity | SAMDC activity |
|---|---|---|---|
| | | (pmol $CO_2$/mg prot/hr) | |
| Control | 3.87 | 7.71 | 7.39 |
| Z-BED, 0.5 mM | 3.06 | 5.3 | 13.54 |
| E-BED, 0.5 mM | 1.60 | 1.0 | 1.30 |

TABLE 3

The effects of Z-BED and E-BED upon the polyamine concentrations in *Pyrenophora avenae*

| | nmol g-1 fwt | | | |
|---|---|---|---|---|
| | Putrescine | Cadaverine | Spermidine | Spermine |
| Control | 62.1 ± 11.1 | 28.5 ± 9.8 | 199.6 ± 11.5 | 47.8 ± 3.4 |
| Z-BED 0.5 mM | 538.3 ± 25.2 | 57.1 ± 22.3 | 135.5 ± 6.2 | 76.5 ± 6.9 |
| E-BED 0.5 mM | 62.0 ± 19.6 | 45.6 ± 17.8 | 116.8 ± 4.9 | 57.4 ± 3.8 |

EXAMPLE 5

Effects of Z-BED and E-BED on powdery mildew infection of barley leaves

Method

Seeds of barley (*Hordeum vulgare* L Golden Promise) were sown in Fison's Levington compost in 36 cm seed trays. Plants were grown in a glasshouse under natural daylight supplemented for 16 h daily by 400 W mercury vapour lamps. The maximum temperature was 24° C. during the day and fell to a minimum of 9° C. at night. Plants at growth stage 12 (second leaf unfolded, Zadok's scale) were used for experiments. First leaves were cut to a length of 7 cm and placed into 9 cm diameter, single vent, plastic petri dishes containing Oxoid No.3 agar supplemented with 0.02% benzimidazole. The tips of the leaves were embedded in the agar and held in place with coverslips. The leaves were inoculated with *Erysiphe graminis hordei* by transfer of conidia from stock plants using a camel hair brush.

Solutions of the inhibitors were made up in 0.01% Tween 20 and adjusted to pH 7.0 using sodium hydroxide. Concentrations of Z-BED and E-BED used were 0.5 and 1.0 mM. A Shandon spray unit was used to apply the inhibitor solution to all leaves except controls, and sprays were applied until run off. In pre-inoculation treatments, the leaves within petri dishes were sprayed with solutions of the inhibitors and left for 2 h before inoculation. In post-inoculation treatments, the leaves were inoculated and sprayed 3 days after inoculation.

After treatment and inoculation, the petri dishes were placed randomly in a controlled environment. The temperature was 18.5° C., falling to 16.5° C. at night, and artificial light was provided by fluorescent tubes for 16 h per day to give a mean irradiance of 251 $\mu$mol $m^{-2}$ $s^{-1}$. Visual assessment of infection was carried out using a standard diagram 12 days after inoculation and recorded as percent leaf area infected.

Results

The results are shown in Table 4 below.

TABLE 4

|  | % powdery mildew infection |
|---|---|
| Control | 31.5 |
| Z-BED, 0.5 mM | 4.2 |
| Z-BED, 1.0 mM | 3.1 |
| E-BED, 0.5 mM | 0.6 |
| E-BED, 1.0 mM | 0.2 |

EXAMPLE 6

Effects of E-BED and Z-BED as inhibitors on infection of potato leaf discs with the blight fungus *Phytophthora infestans*

Method

Potato leaf discs floating on a solution of the inhibitor at a desired concentration were inoculated with the fungus.

Results

The results are shown In Table 5 below.

TABLE 5

|  | Days after inoculation | |
|---|---|---|
| Treatment | 4 | 6 |
| Control | III | III |
| 1 mM Z-BED | I | I |
| 5 mM Z-BED | — | I |
| 1 mM E-BED | I | I |
| 5 mM E-BED | — | I |

TABLE 5-continued

|  | Days after inoculation | |
|---|---|---|
| Treatment | 4 | 6 |

I a few isolated sporophores
II < 50% infection
III > 50% infection

EXAMPLE 7

Comparison of the effects of Z-BED and E-BED with a commercial fungicide on mildew infection of barley.

The fungicide chosen for comparison with the unsaturated putrescines was "Tilt" (Registered Trademark), containing propiconazole as the active ingredient which is used for mildew control.

Method

Barley seedlings (*Hordeum vulgare* L. CV Golden Promise) were sown in Fisons Levington compost in 36 cm seed trays. Plants were grown in a glasshouse under natural daylight supplemented for 16 h daily by 400 W mercury vapour lamps. The maximum temperature was 24° C. during the day and fell to a minimum of 9° C. at night. Plants at growth stage 12 (second leaf unfolded, Zadok's scale) were used In experiments. Seedlings were sprayed to run-off with solutions of E-BED and Z-BED at a concentration of 5 mM containing 0.01% Tween 20. In all cases solutions were adjusted to pH 7.0 prior to spraying (using either sodium hydroxide or HCl). "Tilt" was prepared according to the manufacturer's instructions.

Solutions were sprayed onto seedlings until run off using a Shandon spray unit. Plants were inoculated with powdery mildew conidia by shaking infected stock plants over them. Intensity of infection was assessed 7 and 10 d after inoculation by estimating the percentage leaf area infected using a standard diagram. Sporulation usually occured about 6–7 days after inoculation.

Results

The results are shown in Table 6 below.

TABLE 6

|  | % powdery mildew control (leaves 1,2,3) | |
|---|---|---|
|  | days after inoculation | |
|  | 7 | 10 |
| "Tilt" | 45 | 39 |
| Z-BED | 25 | 25 |
| E-BED | 68 | 62 |

* active ingredient of "Tilt" is propicanozole.
All compounds tested at 5 mM.

EXAMPLE 8

Effects of E-BED and Z-BED on infection of broad beans with the chocolate spot fungus, *Botrytis fabae*.

Method

Seeds of broad bean (*Vicia faba* cv Express Long Pod) were sown in Fison's Levington compost in 15 cm plastic pots. Plants were grown in a ventilated glasshouse under natural daylight supplemented to a 16 h photoperiod with 400 W mercury vapour lamps. The maximum daylight temperature was 24° C., falling to a minimum of 9° C. at night.

Twenty day-old plants were sprayed to run-off with solutions of Z-BED or E-BED (1 or 3 mM) before or after inoculation with spores of *Botrytis fabae*. Solutions were prepared in 0.01% Tween 20, with the pH adjusted to 7.0 with sodium hydroxide. Control plants were sprayed with Tween 20 (0.01%) only. After inoculation with a spore suspension, plants were loosely covered in plastic bags for 48 h to maintain the high relative humidity necessary for spore germination.

Plants to be given a pre-inoculatory treatment were sprayed with the inhibitors and left to dry for 2 h before inoculation. For post-inoculatory treatments, plants were inoculated and left for 2 days before application of the inhibitor. Intensity of infection was assessed 3, 5 and 7 days after inoculation by estimating the percent leaf area infected using a standard area diagram.

Results

The effects of the formulations (Z-BED and E-BED), on infection of bean plants by the necrotrophic fungus, *Botrytis fabae*, were examined. The formulations Z-BED and E-BED reduced infection substantially. The results are shown in Tables 7 and 8 below.

TABLE 7

Effects of a Pre-inoculation spray of E-BED and Z-BED on Infection of Broad Bean by *Botrytis fabae*.

| TREATMENT | % Leaf-Area Infected DAI | | |
|---|---|---|---|
| | 3 | 5 | 7 |
| Control | 1.93 ± 0.55 | 2.1 ± 0.49 | 3.25 ± 0.68 |
| 1 mM Z-BED | 0.52 ± 0.11 | 0.56 ± 0.19 | 0.67 ± 0.11 |
| 3 mM Z-BED | 0.25 ± 0.11 | 0.30 ± 0.08 | 0.52 ± 0.16 |
| 1 mM E-BED | 0.28 ± 0.06 | 0.37 ± 0.09 | 0.50 ± 0.14 |
| 3 mM E-BED | 0.24 ± 0.06 | 0.24 ± 0.08 | 0.25 ± 0.06 |

DAI = Days after inoculation

TABLE 8

Effects of a Post-inoculation spray of E-BED and Z-BED on Infection of Broad Bean by *Botrytis fabae*.

| TREATMENT | % Leaf Area Infected DAI | | |
|---|---|---|---|
| | 3 | 5 | 7 |
| Control | 1.93 ± 0.55 | 2.1 ± 0.49 | 3.25 ± 0.68 |
| 1 mM Z-BED | 0.42 ± 0.22 | 0.43 ± 0.13 | 0.68 ± 0.37 |
| 3 mM Z-BED | 1.96 ± 1.41 | 2.1 ± 0.77 | 2.3 ± 1.3 |
| 1 mM E-BED | 0.47 ± 0.30 | 0.31 ± 0.13 | 0.31 ± 0.12 |
| 3 mM E-BED | 0.21 ± 0.12 | 0.38 ± 0.16 | 0.56 ± 0.24 |

DAI = Days after inoculation

EXAMPLE 9

Effects of E-BED and Z-BED on infection of broad beans with the rust fungus, *Uromyces viciae-fabae*.

Method

These experiments were performed using the method described above for infection of beans with *Botrytis fabae*. For the rust experiments, Z-BED and E-BED were used at 1 and 5 mM concentrations and assessment of intensity of infection was carried out 12, 15 and 18 days after inoculation.

Results

Both of the diamine formulations, E-BED and Z-BED, at the two concentrations tested (1 and 5 mM) substantially reduced rust infection when applied before or after inoculation. The trans-compound, E-BED was consistently more effective than the cis-analogue, Z-BED.

The results are shown in Tables 9 and 10 below.

TABLE 9

Effects of pre-inoculation treatment with E-BED or Z-BED as inhibitors of infection of broad bean with the rust fungus, *Uromyces viciae-fabae*.

| Treatment | % Leaf Area Infected DAI | | |
|---|---|---|---|
| | 12 | 15 | 18 |
| Control | 8.8 ± 1.5 | 15.4 ± 1.9 | 22.5 ± 2.6 |
| 1 mM Z-BED | 5.4 ± 1.1*** | 9.6 ± 1.8*** | 12.9 ± 3.1*** |
| 5 mM Z-BED | 3.6 ± 1.1*** | 7.8 ± 1.9*** | 8.4 ± 2.3*** |
| 1 mM E-BED | 3.2 ± 0.8*** | 10.0 ± 1.8*** | 10.0 ± 2.0*** |
| 5 mM E-BED | 2.8 ± 1.4*** | 5.6 ± 2.2*** | 5.1 ± 2.3*** |

DAI: days after inoculation
Significant differences are shown at $P = 0.001^{*}$, $P = 0.01^{}$, $P = 0.1^{*}$

TABLE 10

Effects of post-inoculation treatment with E-BED or Z-BED as inhibitors of infection of broad bean with the rust, *Uromyces viciae-fabae*.

| Treatment | % Leaf Area Infected DAI | | |
|---|---|---|---|
| | 12 | 15 | 18 |
| Control | 8.8 ± 1.5 | 15.4 ± 1.9 | 22.5 ± 2.6 |
| 1 mM Z-BED | 2.9 ± 0.6*** | 9.2 ± 0.8** | 10.0 ± 1.1*** |
| 5 mM Z-BED | 2.8 ± 0.8*** | 6.7 ± 0.8*** | 9.6 ± 1.6*** |
| 1 mM E-BED | 2.0 ± 0.8*** | 3.7 ± 1.3*** | 6.3 ± 2.6*** |
| 5 mM E-BED | 1.0 ± 0.3*** | 2.7 ± 0.5*** | 4.5 ± 1.1*** |

DAI: days after inoculation
Significant differences are shown at $P = 0.001^{*}$, $P = 0.01^{}$, $P = 0.1^{*}$

EXAMPLE 10

Effects of E-BED and Z-BED on infection of apple with the powdery mildew fungus, *Podosphaera leucotricha*.

Method

Seeds of apple (*Malus bitenfelder*) were stratified by placing in cold store for 14 weeks in trays of Fison's Levington compost. After 14 weeks the seeds were removed from cold storage and after 10 days those which had germinated were potted into individual 4 cm pots. After a further 12 days, the seedlings were inoculated by gently brushing spores of the apple powdery mildew fungus *Podosphaera leucotricha* onto leaves. Three days after inoculation the seedlings were sprayed to run off with a solution of Z-BED or E-BED (3 mM) using a Shandon spray unit. Inhibitor solutions were prepared in 0.01% Tween 20 and the pH adjusted to 7.0 using sodium hydroxide. Intensity of infection was assessed 13, 15 and 17 days after inoculation by estimating the percent leaf area infected.

Results

The unsaturated putrescines gave very good control of mildew infection of apple seedlings. The results are shown in Table 11 below.

TABLE 11

Effects of treatment with E-BED and Z-BED as inhibitors of infection of apple seedlings with the powdery mildew fungus, *Podosphaera leucotricha*

| Treatment | % Leaf Area Infected DAI | | |
|---|---|---|---|
| | 13 | 15 | 17 |
| Control | I | II | III |
| 3 mM Z-BED | 0 | I | I |
| 3 mM E-BED | 0 | I | I |

DAI: days after inoculation
Key
0 = no infection
I = infection only just visible (a few isolated spores)
II = <50% infection
III = >50% infection

EXAMPLE 11

Effects of E-BED on infection of barley seedlings by fungicide resistant strains of powdery mildew.

The effectiveness of 1 mM E-BED on infection of barley seedlings by fungicide resistant strains of powdery mildew was examined. Three strains of fungicide resistant barley powdery mildew were used, all supplied by the John Innes Centre for Plant Science Research, Cambridge Lab, Norwich:

cc-146 resistant to ethirimol and triadimenol cc-138 resistant to triadimenol cc-139 resistant to fenpropidin and fenpropimorph The method of growing the seedlings and applying the compounds was as described in Example 7. The compounds were used at a concentration of 1 mM. "Mistral" and "Bayfidan" fungicides were used at the manufacturer's recommended rates.

The results are shown in Table 12 below.

TABLE 12

Effects of E-BED on infection of barley seedlings by fungicide-resistant strains of powdery mildew

| Mildew strains | % mildew infection | | |
|---|---|---|---|
| | cc-146 | cc-138 | cc-139 |
| Control | 15.1 ± 1.4 | 22.5 ± 1.9 | 17.8 ± 1.2 |
| E-BED, 1 mM | 1.9 ± 0.2 | 2.2 ± 0.3 | 1.7 ± 0.3 |
| Mistral | 0.8 ± 0.1 | 1.5 ± 0.1 | 14.2 ± 1.7 |
| Bayfidan | 12.1 ± 1.0 | 20.9 ± 2.1 | 1.2 ± 0.2 |

E-BED gave very good control of all of the strains of powdery mildew. In contrast, the fungicides "Mistral" (Registered Trade Mark) (containing fenpropimorph) as the active group and "Bayfidan" (Registered Trade Mark) (containing triadimenol) as the active group gave poor control of strains cc-139 and cc-138 respectively.

EXAMPLE 12

Root drench tests for the systemic action of E-BED

When carrying out the root drench tests, barley seedlings (10 per tray) were drenched with 187.5 ml of the compound at a 1 mM concentration. The compound was applied 1, 2 or 5 days before or after inoculation of the seedlings with mildew. When applied as a post inoculation drench, mildew infection was reduced substantially. The effectiveness of E-BED as a post inoculation root drench was greatest if the compound was applied 1 or 2 days after mildew inoculation and was less effective if applied 5 days after inoculation. These results suggest that E-BED is metabolised in the plant, that E-BED and its metabolite(s) have systemic action in the xylem, and that E-BED arriving in the leaf via the xylem is the antifungal agent, while its metabolite(s) have growth-promoting properties. The data on E-BED as a post inoculation root drench indicate that for best inhibition of fungal growth, E-BED must be taken up by the fungus very soon after penetration of the host epidermal cells.

The results are shown in Table 13 below.

TABLE 13

Effects of E-BED applied as a root drench, on mildew infection of barley seedlings
All teatments applied at 1 mM

| Treatment | % mildew infection days after inoculation | | |
|---|---|---|---|
| | 6 | 8 | 10 |
| Pre-inoculation root drench | | | |
| Control | 12.6 ± 1.2 | 25.0 ± 2.4 | 32.5 ± 1.8 |
| E-BED, 1 d pre | 16.5 ± 1.3 | 29.5 ± 2.4 | 42.0 ± 3.5 |
| E-BED, 2 d pre | 29.5 ± 1.8 | 42.0 ± 3.0 | 51.5 ± 2.5 |
| E-BED, 5 d pre | 26.5 ± 1.8 | 34.5 ± 2.1 | 49.5 ± 2.8 |
| Control | 3.5 ± 0.4 | 6.4 ± 0.6 | 8.3 ± 0.8 |
| E-BED, 1 d post | 1.0 ± 0.2 | 1.5 ± 0.2 | 3.5 ± 0.6 |
| E-BED, 2 d post | 1.2 ± 0.3 | 1.8 ± 0.4 | 3.4 ± 0.6 |
| E-BED, 5 d post | 2.4 ± 0.2 | 3.9 ± 0.4 | 6.9 ± 0.7 |

EXAMPLE 13

Field Trials of E-BED

A field trial of the effectiveness of E-BED as a treatment for foliar diseases of barley (mainly powdery mildew) was carried out. E-BED (1 and 5 mM) was tested against DFMO and the ICI fungicide 'Early Impact' (Registered Trade Mark), which contains flutriafol and carbendazim as active anti-fungal agents. The different treatments were applied either as one spray at GS 39 or as two sprays at GS 39 and GS 49. Due to the weather conditions mildew appeared in the crop very early. Thus, the first sprays were applied about 10 days earlier than planned, since mildew was already present at about 5% in the crop. Disease was assessed on the third leaf one and two weeks after spraying. The second spray was also brought forward, since due to favourable weather, crop growth was exceptionally rapid. After the second spray, disease was assessed on the flag leaf one and two weeks after treatment.

Powdery mildew was by far the most prevalent disease in the barley crop and only mildew infection was assessed. Mildew levels had reached nearly 10% in controls one week after spraying and two weeks after treatment there was 20% mildew infection. Although all treatments reduced mildew infection, E-BED was at least as good as Early Impact, reducing mildew substantially. When mildew was assessed on the flag leaf later in the season, plots given only the earlier spray had very high levels of mildew. This was not surprising given the very high numbers of mildew spores above crops. Under the high inoculum pressure, 1 mM E-BED failed to control mildew on the flag leaf, although mildew levels were reduced by 50% on these leaves following a spray with 5 mM E-BED. A second spray of Early Impact gave good control of mildew on the flag leaf.

Thus, E-BED gave excellent early season control of mildew in barley, but under increasingly high inoculum pressures later in the season, only the higher concentration of E-BED reduced mildew. Since E-BED managed to Keep mildew off the crop during the earlier stages of crop growth, yield reductions should be kept to a minimum.

The results are shown in Table 14 below.

TABLE 14

Results of a field trial of the effects of E-BED on powdery mildew infection of a spring barley crop

| Treatment | Assessment 1 | | 2 | | 3 | | 4 | |
|---|---|---|---|---|---|---|---|---|
| | mil | gla | mil | gla | mil | gla | mil | gla |
| One spray | | | | | | | | |
| E-BED, 1 mM | 4.1 | 94.9 | 10.6 | 85.0 | 11.4 | 86.9 | 15.28 | 80.8 |
| E-BED, 5 mM | 3.6 | 95.7 | 10.8 | 79.3 | 8.9 | 89.3 | 17.1 | 79.7 |
| DFMO, 1 mM | 4.5 | 94.8 | 18.95 | 69.6 | 8.48 | 88.5 | 19.4 | 75.5 |
| DFMO, 5 mM | 3.9 | 95.4 | 13.0 | 80.0 | 9.9 | 89.1 | 24.2 | 70.8 |
| Early Impact | 3.6 | 96.4 | 9.2 | 87.1 | 8.5 | 89.0 | 17.9 | 79.3 |
| Two sprays | | | | | | | | |
| E-BED, 1 mM | 4.2 | 92.8 | 13.2 | 79.8 | 7.0 | 90.9 | 13.5 | 83.0 |
| E-BED, 5 mM | 3.4 | 95.7 | 10.5 | 83.2 | 3.5 | 94.2 | 10.2 | 86.4 |
| DFMO, 1 mM | 6.6 | 92.2 | 21.9 | 71.4 | 7.7 | 90.3 | 14.3 | 81.4 |
| DFMO, 5 mM | 2.1 | 97.4 | 11.7 | 82.5 | 7.0 | 91.0 | 15.2 | 80.7 |
| Early Impact | 4.8 | 94.7 | 11.7 | 81.9 | 2.6 | 91.0 | 4.8 | 91.2 |
| Control | 9.5 | 88.8 | 20.2 | 67.2 | 6.4 | 88.6 | 14.0 | 77.5 | mil % powdery mildew infection
gla % green leaf area
Spray one: GS 39 (Zadoks scale)
Spray two: GS 49 (Zadoks scale)
Assessments 1 and 2 were made 1 & 2 weeks after spray 1, respectively
Assessments 3 and 4 were made 1 & 2 weeks after spray 2, respectively The effect on the growth and field of the plants were also investigated. 1 mM E-BED applied either as a single spray or as two sprays, had little effect on plant height, although in both cases plant dry weight was increased. A single spray of 1 mM E-BED reduced grain yield slightly, while two sprays of 1 mM E-BED increased grain yield by 3.3%. E-BED applied at 5 mM, either as one or two sprays, resulted in increased plant height, plant dry weight and grain yield. The increases in plant dry weight and grain yield were larger than those observed with DFMO or Early Impact. Thus, a single spray of 5 mM E-BED gave a 9% increase in grain yield, while two sprays gave a 13% increase in grain yield. These increases could be the result of early season mildew control by E-BED and/or growth promoting effects of the inhibitor.

The results are shown in Table 15 below.

TABLE 15

Field Trial of the effects of E-BED on growth and yield of spring barley.

| Treatment | Plant Height cm | Plant Dry Weight g | Grain Yield g |
|---|---|---|---|
| Control | 75.7 | 7.7 | 6.9 |
| E-BED, 1 mM, 1 spray | 75.4 | 7.9 | 6.3 |
| E-BED, 5 mM, 1 spray | 77.4 | 10.5 | 7.6 |
| DFMO, 1 mM, 1 spray | 73.8 | 8.9 | 6.9 |

TABLE 15-continued

Field Trial of the effects of E-BED on growth and yield of spring barley.

| Treatment | Plant Height cm | Plant Dry Weight g | Grain Yield g |
|---|---|---|---|
| DFMO, 5 mM, 1 spray | 78.0 | 9.0 | 7.1 |
| Early Impact, 1 spray | 78.8 | 9.6 | 7.1 |
| E-BED, 1 mM, 2 sprays | 75.8 | 8.5 | 7.1 |
| E-BED, 1 mM, 2 sprays | 81.0 | 11.8 | 7.9 |
| DFMO, 1 mM, 2 sprays | 74.1 | 8.7 | 6.9 |
| DFMO, 1 mM, 2 sprays | 76.7 | 10.6 | 7.5 |
| Early Impact | 80.8 | 9.7 | 7.9 |

EXAMPLE 14

Effects of the timing of the application of E-BED on the control of barley powdery mildew The method of growing barley seedlings and carrying out the experiment was as described in Example 7, except that E-BED was applied to the barley seedlings at different times before or after inoculation with the pathogen in concentrations of 1 mM. The intensity of infection was assessed 6, 8 and 10 days after inoculation.

The results are shown in Table 16 below.

TABLE 16

Effects of application of E-BED at different times before or after inoculation, on powdery mildew infection of barley seedlings. All compounds applied at 1 mM. Assessments were made 6, 8 and 10 days after inoculation, but only the assessment on day 10 is shown.

| | % mildew infection |
|---|---|
| Control | 15.8 ± 1.7 |
| 5 d pre-inoculation E-BED | 5.0 ± 0.4 |
| 2 d pre-inoculation E-BED | 5.2 ± 1.5 |
| 1 d pre-inoculation E-BED | 5.1 ± 1.3 |
| 1 d post-inoculation E-BED | 3.5 ± 0.4 |
| 2 d post-inoculation E-BED | 3.9 ± 0.8 |
| 5 d post-inoculation E-BED | 5.0 ± 0.4 |

All treatments with E-BED gave very large reductions in mildew infection although the best control was obtained if E-BED was applied 1 or 2 days after inoculation with the fungus. This confirms that E-BED has preventative and curative action.

EXAMPLE 15

Effects of E-BED salts on mildew infection of barley seedlings

E-BED salts were synthesised as described in Examples 1–4 and were tested for their effects on mildew infection of barley seedlings by the procedure described in Example 7. The results are shown in Table 17 below. All compounds were applied as post-inoculation sprays at 1 mM. Mildew infection was assessed at 8 days after inoculation.

TABLE 17

| | % mildew infection on barley | % control |
|---|---|---|
| Control | 32.0 ± 2.5 | |

TABLE 17-continued

| | % mildew infection on barley | % control |
|---|---|---|
| E-BED benzoate | 13.7 ± 0.6 | 58 |
| E-BED phosphate | 12.9 ± 0.7 | 60 |
| E-BED fumarate | 10.5 ± 0.8 | 68 |
| E-BED propionate | 11.6 ± 0.8 | 64 |
| E-BED | | 62–99 |

We claim:

1. A method of fungicidal treatment of plants comprising treating plant material with a fungicidally effective amount of (E)-2-butene-1,4-diamine or a salt thereof.

2. A method according to claim 1 wherein said plant materials are seeds.

3. A method according to claim 1 wherein said plant materials are leaves.

4. A method according to claim 1 wherein said plant materials are stems.

5. A method according to claim 1 wherein said plant materials are fruits.

6. A method according to claim 1 wherein said plant materials are growing plants.

7. A method according to claim 1 wherein said plant materials are harvested plant materials.

8. A method of preventing fungal infection in harvested plant materials comprising treating packaging for the harvested plant with a fungicidally effective amount of (E)-2-butene-1,4-diamine or a salt thereof.

9. A method of fungicidal treatment of plants, comprising treating soil in which plants are growing or will be grown with a fungicidally effective amount of (E)-2-butene-1,4-diamine or a salt thereof.

* * * * *